(12) United States Patent
Jolliffe

(10) Patent No.: US 6,589,551 B1
(45) Date of Patent: Jul. 8, 2003

(54) CHEWABLE ORAL UNIT DOSAGE

(75) Inventor: Ian Gordon Jolliffe, Cottingham (GB)

(73) Assignee: Reckitt Benckiser Healthcare (UK) Limited, Slough (GB)

( * ) Notice: Subject to any disclaimer, the term of this patent is extended or adjusted under 35 U.S.C. 154(b) by 0 days.

(21) Appl. No.: 09/720,349

(22) PCT Filed: Jun. 10, 1999

(86) PCT No.: PCT/GB99/01851

§ 371 (c)(1),
(2), (4) Date: Feb. 19, 2001

(87) PCT Pub. No.: WO00/01372

PCT Pub. Date: Jan. 13, 2000

(30) Foreign Application Priority Data

Jul. 2, 1998 (GB) ............................................. 9814234

(51) Int. Cl.[7] .................................................. A61K 9/48
(52) U.S. Cl. ........................ 424/451; 424/456; 424/455
(58) Field of Search ................................. 424/439, 441, 424/451, 440, 456, 455

(56) References Cited

FOREIGN PATENT DOCUMENTS

| DE | 196 52 257 A1 | 6/1998 | ............. A61K/9/00 |
|----|---------------|--------|------------------------|
| EP | 0 211 079 A1 | 1/1985 | ............. A61K/7/00 |
| EP | 0 211 079 A1 | 2/1987 | ............. A61K/7/00 |
| EP | 0 228 067 A2 | 7/1987 | ............. A61J/3/07 |
| EP | 0 308 637 A1 | 3/1989 | ............. A61K/9/48 |
| GB | 2 148 841 A | 6/1985 | ............. A61K/9/48 |
| WO | 88/03803 | 6/1988 | ......... A61K/31/465 |

OTHER PUBLICATIONS

Copy of PCT International Search Report for PCT/GB99/01851 dated Jan. 14, 2000.

Copy of GB Search Report for GB Application No. 9814234.2 dated Oct. 26, 1998.

Primary Examiner—James M. Spear
(74) Attorney, Agent, or Firm—Fish & Richardson P.C.

(57) ABSTRACT

An oral unit dosage comprising a substrate defining a plurality of discrete reservoirs each containing a liquid fill for release in the mouth.

20 Claims, 1 Drawing Sheet

CHEWABLE ORAL UNIT DOSAGE

This application is a 371 of PCT/GB99/01851 filed Jun. 10, 1999.

BACKGROUND OF THE INVENTION

This invention relates to chewable capsules having improved acceptability for the consumer.

Soft gelatin capsules are a well established means for providing a variety of liquid products such as drugs or dietary supplements in a relatively digestible form.

EP 0211079 discloses a partitioned soft capsule in which a rapidly soluble film is used to form both parts of a capsule. The capsule is able to deliver two separate liquid compositions which are contained within separate but adjacent reservoirs in the capsule to the mouth. The capsules of this patent suffer the disadvantage that they are not easy to grip between the teeth when chewing and are thus prone to "popping out" from between the teeth as the patient bites the capsule. In addition, it is necessary to form the capsule from at least three separately fed sheets of material thereby increasing the complexity of manufacture and hence the cost per capsule.

When chewable capsules are chewed or bitten (rather than swallowed), they release their contents into the mouth. This may be particularly advantageous when the capsule contents have a topical effect in the mouth or throat or when the liquid fill provides a soothing or coating effect. Delivering liquids by this means is particularly useful when bulk doses of liquid medicaments are not convenient (e.g. because of frequent or irregular dosing patterns or when measuring doses accurately is not convenient).

Chewable capsules may also be particularly advantageous when the patient is unable or unwilling to swallow solid dosage forms (e.g. tablets or hard capsules) e.g. because of age, throat pain/constriction etc.

The full commercial development of such chewable dosage forms has however been hindered by two particular drawbacks.

Firstly, for capsules above a volume of approximately 0.5 ml, when the capsule is bitten the resulting burst of contents is aesthetically unpleasant, indeed it has been likened to "biting an eyeball". To overcome this drawback it has been suggested that the fill volume of the capsules should be reduced, but this is not always practical. To reduce the fill volume whilst delivering the same drug dosage the fill must be more concentrated, which in most cases means more viscous. Increasing viscosity leads to difficulty in filling the capsules accurately (as the fill must be pumped through narrow dosing tubes) and consequent unacceptable dose variations. Also small capsules are difficult to locate between the teeth and are therefore difficult to break open.

A second disadvantage of conventional chewable capsules is that many active materials or excipients are incompatible with each other when combined in a liquid fill. This incompatibility may be due to reactions between two or more components of the liquid fill, leading to e.g. degradation of one or more of the active materials, or the release of gases which cause the capsules to burst. This means that for many combinations of active, materials and or excipients it is necessary to provide two or more different capsules each time a dose is taken; increasing the risk of confusion of the patient and poor compliance with the correct dosing schedule.

There is thus a need for a chewable capsule which is capable of delivering one or more liquid compositions to the mouth without the unpleasant sensation of the contents spurting out that occurs when a conventional capsule is bitten. It is also desirable for the chewable capsule to be suitable for delivering two or more incompatible liquid formulations to the patient via a single oral dosage form. Ideally, the chewable capsules should have a simple construction and be inexpensive to manufacture. The present invention aims to provide a chewable capsule satisfying the above aims and having a mouth feel which is acceptable to the patient.

SUMMARY OF THE INVENTION

According to the present invention there is provided a chewable oral unit dosage for releasing liquid in the mouth, comprising a soft ingestible substrate which includes a plurality of spatially-separated reservoirs, wherein each reservoir is adapted to retain liquid fills, preferably discrete liquid fills, and wherein the release of the liquid fills from the reservoirs occurs in a controlled manner when he unit dosage is chewed.

Preferably the oral unit dosage is a capsule, more preferably a gelatin capsule.

Figure 1:
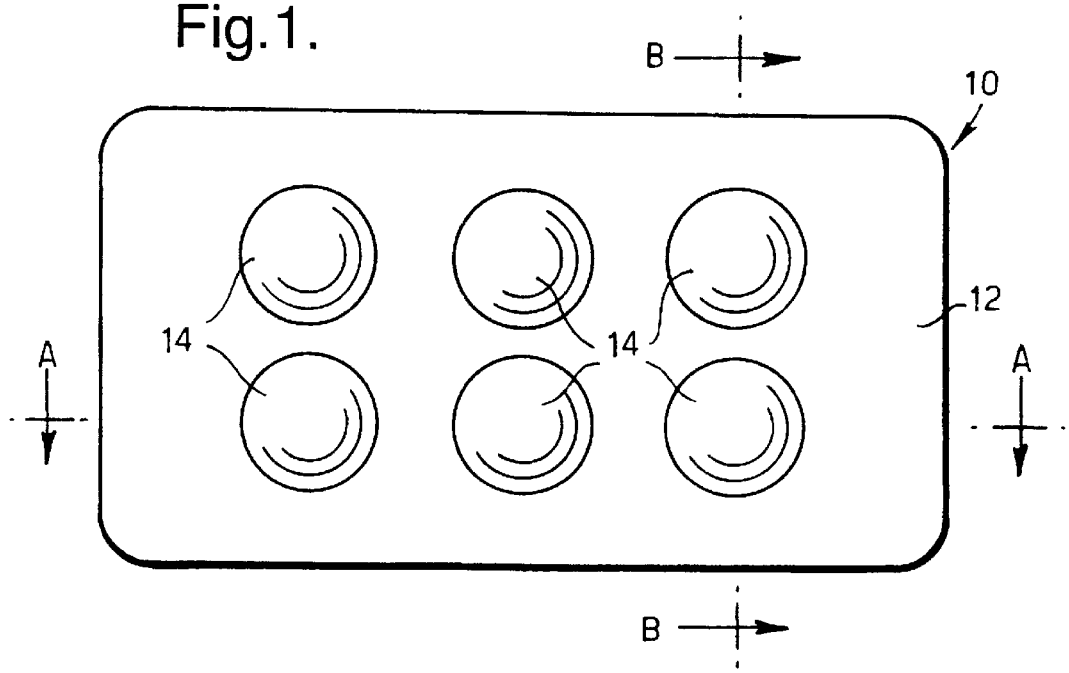
FIG. 1 is a plan view of an oral unit dosage according to the invention.
Figure 2:
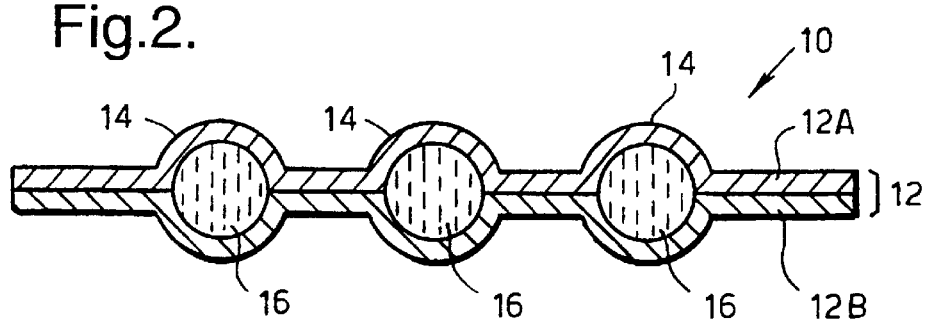
FIG. 2 is a side view cross section (A—A) of an oral unit dosage according to the invention.
Figure 3:
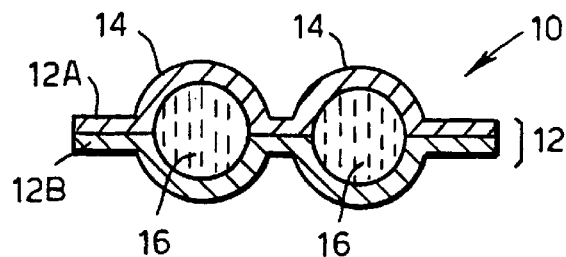
FIG. 3 is an end view cross section (B—B) of an oral unit dosage according to the invention.

By controlled manner it is meant that, whether or not more than one liquid fill composition is used in the same capsule, the normal liquid fill volume is divided between a number of smaller reservoirs with the result that only a few reservoirs are burst in any one bite and the sudden burst of a large volume of liquid fill will be avoided.

The individual discrete reservoirs are non interconnecting and are spaced apart from one another.

Preferably in the oral unit dosages of the invention each reservoir has substantially the same volume.

Preferably the volume of each of the reservoirs in the oral unit dosages of the invention is not more than 0.5 ml, more preferably it is from 0.05 to 0.5 ml and most preferably from 0.1 to 0.35 ml.

Preferably the substrate of the oral unit dosages or the invention comprise from 2 to 30 reservoirs, more preferably from 5 to 20, and most preferably from 10 to 15.

Optionally the oral unit dosages of the invention may contain at least two different liquid fills in different reservoirs. The different liquid fills may separately contain components that would be incompatible if they were combined in a single liquid fill, for example two incompatible active materials or an active material and an incompatible excipient.

Examples of incompatible components include acids and bases; for example alginic acid and sodium bicarbonate, cetylpyridinium chloride and ascorbic acid, cimetidine and sodium bicarbonate, effervescent couples (e.g. citric acid and sodium bicarbonate), aspartame (a sweetener) and magnesium trisilicate (an antacid), cimetidine and vanilla (a flavouring agent), or benzocaine and cherry flavour.

It is possible in the oral unit dosages of the invention that the walls of the reservoirs are composed of a different material from the substrate in which they are embedded. However, it is preferred that the reservoir walls are composed of the same material as the substrate, i.e. the reservoirs are merely spaces in the substrate produced by the insertion of and/or including the liquid fill(s).

Thus, the oral unit dosages of the invention preferably consist essentially only of two components, the substrate and one or more liquid fills plus, optionally, a coating agent.

The substrate may comprise any film-forming material suitable for forming chewable capsules, for example suitably treated starch, cellulose or derivatives thereof or gelatin. Preferably the substrate comprises gelatin.

The substrate may further comprise agents to improve its handling or organoleptic properties, for example plasticisers (e.g. glycerine, sorbitol or propylene glycol, in amounts of up to 50%, more preferably 20–35%, by weight of the substrate); water (up to 50%, more preferably 30–40%, by weight of the substrate); preservatives (e.g. potassium sorbate or methyl, ethyl or propyl parabens); dyes; opacifiers; flavours; or additional drug substances.

The liquid fill will comprise either a solid active material that has been dissolved, solubilised, or dispersed (with suspending agents such as beeswax, hydrogenated caster oil or polyethylene glycol 4000), or a liquid active material; in vehicles or combinations of vehicles such as mineral oil, vegetable oils, triglycerides, glycols, polyols, and surface active agents.

The liquid fill may optionally also comprise flavouring agents, sweeteners or powdery materials to improve the mouth feel of the fill once the reservoirs are broken open (e.g. bulk sweeteners such as sucrose or mannitol).

The selection of appropriate substrate materials plus excipients and fill materials will be obvious to one skilled in the art of chewable capsule production, and will depend largely upon the active material being delivered by the oral unit dosage of the invention.

It will be appreciated that, when the amount of fill material dosed into each reservoir is fairly low, care should be taken to ensure that the fill is not too viscous for accurate dosing. This will not be such a problem as in the production of single low volume capsules as the concentration of active agent will not need to be so high as in such capsules.

Suitable active materials for use in the oral unit dosages of the invention include any materials that may be formulated in a liquid fill, for example:

a) systemically acting agents, such as histamine $H_2$ receptor antagonists (e.g. ranitidine), proton pump inhibitors (e.g. omeprazole), prokinetic agents (e.g. metoclopramide), antidiarrhoeal agents (e.g. loperamide), laxatives (e.g. senna powder), non seroidal anti-inflammatory agents (e.g. naproxen, diclofenac, ibuprofen and aspirin) or decongestants (e.g. pseudoephedrine);

b) materials acting locally in the mouth, such as local antimicrobial agents (e.g. cetyl pyridinium chloride, hexyl resorcinol, triclosan), local anaesthetics (e.g. lignocaine hydrochloride, benzocaine) anti-inflammatory agents (e.g. aspirin, benzydamine, ketoprofen) steroids (e.g. hydrocortisone), topical antibiotics (e.g. tyrothricin, fusafungine, nystatin), decongestants (e.g. phenylephrine hydrochloride) or antihistamines (e.g. terfenadine);

c) materials acting locally in the throat or oesophagus, such as cough suppressants (e.g. dextromethorphan), expectorants (e.g. guiaphenesin), antacids (e.g. calcium carbonate, sodium bicarbonate), or soothing/coating agents (e.g. sodium alginate or dimethicone.

Suitable materials that may optionally be used to coat the oral unit dosages of the invention include cellulose derivatives such as hydroxy ethyl cellulose, hydroxy methyl cellulose or hydroxy propyl cellulose.

The oral unit dosages of the invention may be manufactured by any of the methods normally used for the production of chewable capsules having low fill volumes (taking into account the materials selected), with the special adaptation that the encapsulated dosages are not separated individually but are divided up so that each dosage comprises a plurality of discrete reservoirs. The method of manufacture may be further adapted so that each of the individual reservoirs has a volume of less than 0.5 ml and/or so that two or more different liquid fills are included in different reservoirs within the same oral unit dosage.

Commercial methods for producing chewable capsules include the plate process and the rotary die encapsulation process.

Example of the use of both the plate process and rotary die encapsulation machines are give in, for example, Soft Gelatin Capsules: A Solution To Many Tableting Problems by H. Seager in Pharmaceutical Technology, September 1985, 84–104; and Soft Gelatin Capsules by J. P. Stanley in Theory and Practice of Industrial Pharmacy Eds Lachman L, Lieberman H A, Konig J L, 405–420, 1976.

The invention will now be described with reference to the drawings in which:

In the Figures, the oral unit dosage 10 includes a flat gelatin laminate 12 consisting of two separate gelatin cards 12A and 12B laminated together. The gelatin laminate 12 includes six discrete, sealed, reservoirs 14 which are non-interconnecting and are spaced apart from one another. Each reservoir 14 is filled with liquid fill 16.

When the unit dosage is chewed, only a few reservoirs will burst yielding their liquid fill in any one bite with the result that a sudden burst of a large volume of liquid fill is avoided.

The invention will now be illustrated by reference to the following examples:

EXAMPLE 1

| Liquid Fill | mg Per Capsule |
|---|---|
| Calcium Carbonate | 500 |
| Sodium Bicarbonate | 100 |
| Fractionated Coconut Oil | 600 |
| Lecithin | 12 |
| Colloidal Silicon Dioxide | 34 |
| Sorbitan Fatty Esters | 34 |
| Polysorbate 80 BP | 20 |
| Flavours/Colours/Sweeteners | 80 |
| | 1380 mg (1.2 ml) |

| Capsule Material | % by Weight |
|---|---|
| Gelatin | 40 |
| Glycerin | 25 |
| Water | 35 |
| Mint Flavour | qs |
| Sweetener | qs |
| Colour | qs |

The oral unit dosages are prepared on a conventional rotary die encapsulation machine adapted to provide an individual fill volume of 0.1 ml; and further adapted so that the encapsulated reservoirs are not individually cut off but are divided up in blocks of 12 reservoirs i.e. each oral unit dosage comprises a single piece of gelatin defining twelve reservoirs each having a liquid fill of 0.1 ml.

The resultant chewable capsules deliver an antacid material to the throat and oesophagus without the "chalky" characteristics normally associated with conventional antacid tablets. The capsules are pleasant to chew and do not produce an unpleasant burst effect upon biting.

EXAMPLE 2

| Liquid Fill 1 | mg per capsule |
|---|---|
| Calcium carbonate | 100 |
| Sodium bicarbonate | 100 |
| Lecithin | 12 |
| Fractionated coconut oil | 600 |
| Colloidal silicon dioxide | 34 |
| Sorbitan fatty ester | 34 |
| Poly sorbate 80 | 20 |
| Flavours/Colours/Sweeteners | 80 |
| | 1380 mg (1.2 ml) |

| Liquid Fill 2 | mg per capsule |
|---|---|
| Alginic acid | 500 |
| Lecithin | 12 |
| Fractionated coconut oil | 600 |
| Colloidal silicon dioxide | 34 |
| Sorbitan fatty esters | 34 |

-continued

| Liquid Fill 2 | mg per capsule |
|---|---|
| Polysorbate 80 | 20 |
| Flavours/Colours/Sweeteners | 80 |
| | 1380 mg (1.2 ml) |

Capsule Material

As example 1

The oral unit dosages are prepared as in Example 1 with the further adaptation that the two liquid fills are delivered separately to the capsules, such that each oral unit dosage comprises a single piece of gelatin defining twelve reservoirs each of 0.1 ml volume, six of the reservoirs containing liquid fills and six containing liquid fill 2.

Two capsules of Example 2 provide a full dose of alginic acid which will form a raft on contact with the stomach contents to treat heartburn, gastritis or dyspepsia.

When chewed the capsules of example 2 have a pleasant mouth feel and do not give a sudden unpleasant burst of fill material.

What is claimed is:

1. A chewable oral unit dosage for releasing liquid in the mouth, said dosage comprising a soft ingestible substrate which comprises from 2 to 30 spatially-separated reservoirs, wherein each reservoir has a volume of not more than 0.5 ml and contains a liquid fill and wherein release of the liquid fill from the reservoirs occurs in a controlled manner when the unit dosage is chewed.

2. An oral unit dosage according to claim 1 wherein the plurality of reservoirs contain 2 or more different liquid fills.

3. An oral unit dosage form according to claim 1 wherein the volume of each reservoir ranges from 0.05 to 0.5 ml.

4. An oral unit dosage according to claim 3 wherein the volume of each reservoir ranges from 0.1 to 0.35 ml.

5. An oral unit dosage according to claim 1 wherein the substrate comprises from 5 to 20 reservoirs.

6. An oral unit dosage according to claim 5 wherein the substrate comprises from 10 to 15 reservoirs.

7. An oral unit dosage according to claim 1 wherein the substrate comprises an ingestible film-forming material.

8. An oral unit dosage according to claim 7 wherein the reservoir walls are composed of the same material as the substrate.

9. An oral unit dosage according to claim 7 wherein the film-forming material is gelatin.

10. An oral unit dosage according to claim 1 wherein the liquid fill composition comprises one or more active agents selected from the group consisting of systemically active agents, materials acting locally in the mouth and materials acting locally in the throat or oesophagus.

11. An oral unit dosage according to claim 10 wherein the liquid fill composition comprises a systemically active agent selected from the group consisting of histamine $H_2$ receptor antagonists, proton pump inhibitors, prokinetic agents, antidiarrhoeal agents, laxatives, non-steroidal anti-inflammatory agents, decongestants and pharmaceutically compatible mixtures thereof.

12. An oral unit dosage according to claim 11 in which the systemically active agents are selected from the group consisting of ranitidine, omeprazole, metoclopramide, loperamide, senna powder, naproxen, diclofenac, ibuprofen, aspirin, pseudoephedrine and pharmactically compatible mixtures thereof.

13. An oral unit dosage according to claim 10 wherein the liquid fill composition comprises materials acting locally in the mouth, said materials selected from the group consisting of local antimicrobial agents, local anaesthetics, anti-inflammatory agents steroids topical antibiotics, decongestants, anti-histamines and pharmaceutically compatible mixtures thereof.

14. An oral unit dosage form according to claim 13 in which the materials acting locally in the mouth are selected from the group consisting of cetylpyridinium chloride, hexyl resorcinol, lignocaine hydrochloride, benzocaine, aspirin, benzydamine, ketoprofen, hydrocortisone, tyrothricin, fusafungine, nystatin, phenylephrine hydrochloride, terfenadine and pharmaceutically acceptable mixtures thereof.

15. An oral unit dosage according to claim 10 wherein the liquid fill composition comprises materials acting locally in the throat or oesophagus, said materials selected from the group consisting of cough suppressants, expectorants, antacids, soothing or coating agents and pharmaceutically compatible mixtures thereof.

16. An oral unit dosage according to claim 13 in which the materials acting locally in the throat or oesophagus are selected from the group consisting of dextromethorphan, guiaphenesin, calcium carbonate, sodium bicarbonate, sodium alginate, dimethicone and pharmaceutically acceptable mixtures thereof.

17. An oral unit dosage according to claim 10 wherein the substrate further comprises one or more of plasticisers, water, preservatives, dyes, opacifiers, flavours, additional active agents and sweeteners.

18. An oral unit dosage form according to claim 17 wherein the active agents in the liquid fill compositions are dissolved, solubilised, emulsified and/or dispersed.

19. An oral unit dosage according to claim 18 wherein each of the reservoirs contains calcium carbonate and sodium bicarbonate.

20. An oral unit dosage form according to claim 18 wherein at least one of the reservoirs contains calcium carbonate and sodium bicarbonate and at least one of the reservoirs contains alginic acid.

* * * * *

UNITED STATES PATENT AND TRADEMARK OFFICE
CERTIFICATE OF CORRECTION

PATENT NO.   : 6,589,551 B1
DATED        : July 8, 2003
INVENTOR(S)  : Ian Gordon Jolliffe It is certified that error appears in the above-identified patent and that said Letters Patent is hereby corrected as shown below:

<u>Title page,</u>
Item [86], replace "Feb. 19, 2001" with -- Feb. 15, 2001 --

<u>Column 6,</u>
Line 43, insert -- form -- between "dosage" and "according"

<u>Column 7,</u>
Line 3, replace "pharmactically" with -- pharmaceutically --
Line 10, insert -- , -- after "agents"

Signed and Sealed this

Twenty-seventh Day of January, 2004

JON W. DUDAS
*Acting Director of the United States Patent and Trademark Office*